United States Patent
Claps et al.

(10) Patent No.: US 7,602,488 B2
(45) Date of Patent: Oct. 13, 2009

(54) HIGH-SPEED, RUGGED, TIME-RESOLVED, RAMAN SPECTROMETER FOR SENSING MULTIPLE COMPONENTS OF A SAMPLE

(75) Inventors: Ricardo Claps, San Jose, CA (US); Bradley A. Smith, San Jose, CA (US)

(73) Assignee: Neptec Optical Solutions, Inc., Fremont, CA (US)

( * ) Notice: Subject to any disclaimer, the term of this patent is extended or adjusted under 35 U.S.C. 154(b) by 446 days.

(21) Appl. No.: 11/452,129

(22) Filed: Jun. 12, 2006

(65) Prior Publication Data

US 2007/0285658 A1    Dec. 13, 2007

(51) Int. Cl.
*G01J 3/44* (2006.01)
(52) U.S. Cl. .................................................. 356/301
(58) Field of Classification Search ............... 356/301; 250/227.23, 230, 232, 236
See application file for complete search history.

(56) References Cited

U.S. PATENT DOCUMENTS

| | | | |
|---|---|---|---|
| 5,296,711 A * | 3/1994 | Leonard et al. | ............. 250/372 |
| H2002 H | 11/2001 | McLachlan et al. | |
| 6,377,346 B1 * | 4/2002 | Vaisala et al. | ............... 356/417 |
| 6,483,581 B1 | 11/2002 | Ben-Amotz et al. | |
| 6,734,963 B2 | 5/2004 | Gamble et al. | |
| 6,780,880 B1 | 8/2004 | Whittle et al. | |
| 6,795,177 B2 | 9/2004 | Doyle | |
| 6,859,581 B1 | 2/2005 | Smith et al. | |
| 6,897,951 B2 | 5/2005 | Womble et al. | |
| 7,242,468 B1 * | 7/2007 | Zhang | ........................ 356/301 |

| | | | |
|---|---|---|---|
| 2006/0142650 A1 | 6/2006 | Lodder et al. | |
| 2007/0057211 A1 * | 3/2007 | Bahlman et al. | ............ 250/584 |

OTHER PUBLICATIONS

Notification of Transmittal of the International Search Report in correspoding International Application No. PCT/US07/70653 Dated Apr. 10, 2008 (1 page).
Internatioanl Search Report in corresponding International Application No. PCT/US07/70653 dated Apr. 10, 2008 (2 pages).
Written Opinion of the International Searching Athority in corresponding Internaitonal Application No. PCT/US07/70653 dated Apr. 10, 2008 (7 pages).

\* cited by examiner

*Primary Examiner*—Kara E Geisel
(74) *Attorney, Agent, or Firm*—Haynes and Boone, LLP

(57) ABSTRACT

A new architecture for implementing a time-resolved Raman spectrometer is 2-3 orders of magnitude faster than current systems. The system additionally is compact, environmentally rugged, low cost and can detect multiple components of a sample simultaneously. In one embodiment, the invention employs a rotating optical switch to time multiplex an input signal through multiple bandpass filters and into a single optical detector which is electrically activated only when the filtered input light pulse is about to impact it.

The combination of time-multiplexing the input signal through multiple optical filters and time-sequencing the optical detector enables the device to detect and analyze 2-3 orders of magnitude faster than current designs, processing spectra within milliseconds instead of seconds. The system can process multiple material samples (25+) simultaneously, instead of sequentially, and its mechanical ruggedness and simplicity enables using the system in harsh physical environments when traditional spectrometers can not be used reliably.

12 Claims, 9 Drawing Sheets

Fiber delivery/collection, with optical circulator

Free space signal collection

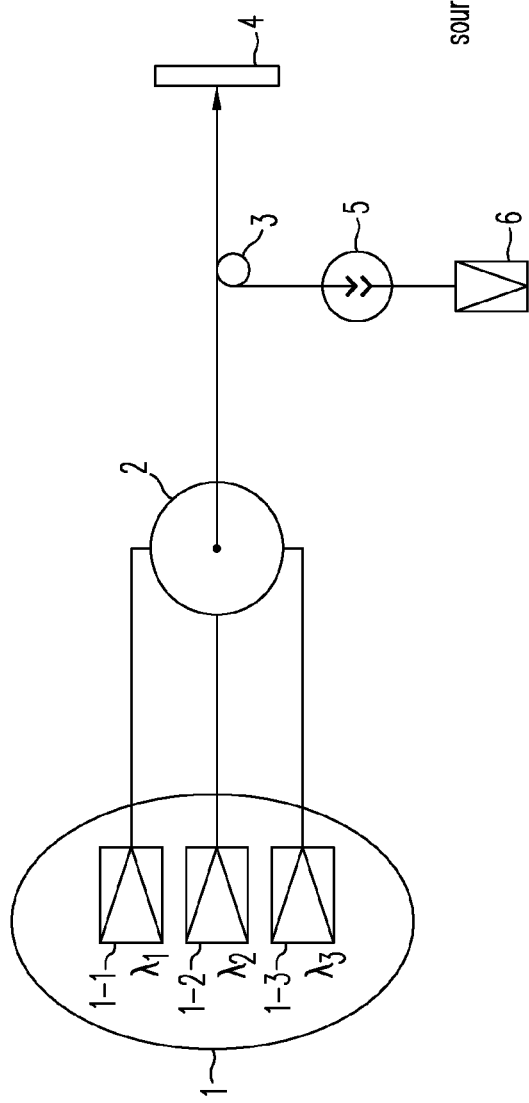
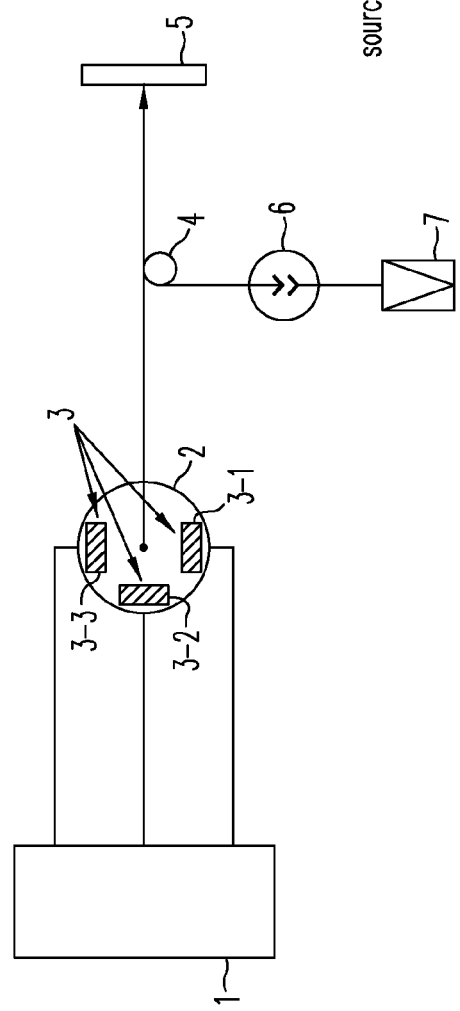
Multiple illumination sources/multiple pump lasers
FIG. 5a
Multiple illumination sources/Emission lamp with filters
FIG. 5b Coarse/Fine spectral coverage

HIGH-SPEED, RUGGED, TIME-RESOLVED, RAMAN SPECTROMETER FOR SENSING MULTIPLE COMPONENTS OF A SAMPLE

FIELD OF THE INVENTION

This invention relates to a time-resolved Raman spectrometer that is two to three orders of magnitude faster than current Raman spectrometers and which is environmentally rugged, low cost and can detect multiple components of a sample simultaneously.

BACKGROUND OF THE INVENTION

Raman spectroscopy is a proven technology in bio-medical, chemical, industrial and other sensing applications. However, significant problems exist for implementing this technique, such as detector sensitivity, processing speed, simultaneous multi-component analysis of a single sample, environmental ruggedness, and cost. In order to obtain Raman spectra from a sample, a high intensity optical source is needed (typically a laser) to pump the inelastic Raman scattering process within the material, be it a gas, a liquid, or a solid. As a result, the material scatters radiation, in all directions, at different frequencies. The component with frequency equal to that of the pump laser corresponds to Rayleigh scattering, and the component with frequency shifted lower than that of the pump laser is called Stokes radiation, a portion of which corresponds to Raman scattering. The main feature of Raman scattering is that it occurs regardless of the wavelength of the pumping optical source, while keeping the frequency shift between Stokes and pump radiation fixed. The Stokes radiation shift and intensity are dependent upon the material. Typically, Stokes Raman shifts are in the order of a few to tens of tera-Hertz (THz), and their intensity is 4 to 5 orders of magnitude lower than the Rayleigh scattered light. In order to discriminate and measure accurately the Raman scattered radiation from the Rayleigh radiation, a blocking filter for the Rayleigh frequency needs to be used in all Raman measurement systems. Fortunately, the typical Raman Stokes shift is large enough to allow for current state-of-the-art filters to block the Rayleigh radiation while marginally affecting the Raman Stokes radiation.

Time-resolved Raman spectroscopy techniques have been used for years. Detection and analysis of the signal in these systems is typically difficult and expensive. Commercial Raman spectrometers are:

1) too slow for many practical applications, with signal processing time of a few seconds or more. Real-time process monitoring is impossible, as are many medical and in-vivo applications;

2) typically limited to measuring no more than two or three components within a given sample, at a time, due to high spectral overlap between different analytes;

3) physically sensitive to the environment such as movement, vibration, and temperature changes, in their performance; and 4) not optically sensitive for many applications such as detecting weak markers in biological samples or weak returns and noisy signals from long-range sensing applications.

Techniques for processing multiple components, in the order of 20 to 100, with a 1 to 10 second typical collection for each, require an excessive amount of time to complete a full sample analysis. Weak signals from noisy environments result in the loss of important spectral information in many cases. Field applications in harsh environments are also off limits for currently available Raman systems.

The most popular types of spectrometers in use today are Fourier-Transform type devices. Fourier Transform Infra-red (FTIR) and Fourier Transform Raman (FTR) spectrometers employ a motor to create a linear displacement of sensitive optical elements in the detection process. This technique has serious operational and environmental limitations, since alignment must be maintained as optical parts are being moved, and also time-calibration is necessarily complex since non-uniform linear motion is involved.

Accordingly, there is a need for simpler, environmentally insensitive Raman spectrometers capable of determining multiple components in a sample within a very short time.

SUMMARY

The present invention provides an environmentally rugged system that performs high-speed Raman spectroscopy with dramatically improved processing speed, enabling the monitoring of multiple components of a sample in a very short time. One embodiment of the system includes the unique ability to process and analyze an individual material sample with a time resolution of 1 ms to 100 ms. This is two to three orders of magnitude faster than currently available commercial devices, which operate at more than 1 second per sample.

By using an ultra-sensitive photo-detector to enhance the system's sensitivity at high speed, the system provides the same sensitivity as current state-of-the-art devices Raman spectrometers but at a much higher speed. The system provides a simple time-calibration of the signal from the sample, therefore improving the accuracy of data collection at a reduced cost.

The system can quantitatively determine a mixture composed of multiple components (for example 20 to 25 or more components), simultaneously.

An embodiment of the system is field-deployable, suitable to be used in moving vehicles and aircraft, and hostile physical environments, with no degraded performance. Thus the system can operate in any given orientation relative to the ground, with no need for readjustments due to gravity.

In its simplest form, the system represents a factor of ten (10) manufacturing cost reduction, relative to similar instruments, due to the reduced number of parts used and simplicity of construction. In particular, the system eliminates the use of gratings, prisms, and other dispersive elements that are lossy, expensive, and extremely sensitive to alignment. As part of the cost reduction, the system uses a single photo-sensitive element, replacing the need for expensive photo-detector arrays and CCD cameras, and simplifying data collection schemes.

An embodiment of the system provides a wide detection bandwidth, being able to detect signals with bandwidths from 900 nm to 2.1 µm.

An embodiment of the system uses a linear regression algorithm to process the data obtained from the sample, thereby reducing the number of data points to be processed by an order of magnitude. The algorithm is a discretized version of Principal Component Analysis techniques (dPCA).

In one embodiment, the system can be directly adapted to perform resonance Raman spectroscopy by introduction of a UV emitting diode in the system, therefore increasing the sensitivity of the system by 2 to 3 orders of magnitude.

The system makes possible a method to perform time-resolved Raman analysis of blood vessel angiography and also makes possible a method for fast detection of calcified plaque in a blood vessel, for real-time diagnosis. Also the Raman spectroscopy system of this invention provides real-time, non-invasive temperature measurements of samples in-vivo or for other applications.

In particular, this invention allows one to determine multi-component concentrations in a given sample, whether a solid, a powder, a liquid, or a gas, using Raman spectroscopy and linear regression techniques.

This invention will be more completely understood in conjunction with the following detailed description taken together with the drawings.

DESCRIPTION OF THE DRAWINGS

FIG. 5a shows an embodiment of this invention using multiple illumination sources and multiple pump lasers.

FIG. 5b shows an embodiment of this invention using multiple illumination sources and an emission lamp with filters.

DETAILED DESCRIPTION

The following detailed description is meant to be illustrative only and not limiting. Other embodiments of this invention will be obvious to those skilled in the art in view of this description.

In accordance with this invention a Raman spectrometry device architecture is provided that combines a high speed time-division optical sampling engine with a unique data processing algorithm, discrete Principal Component Analysis (dPCA), in order to produce time-resolved, accurate Raman measurements with low signal levels. A variety of specific embodiments can be provided to implement the invention. The invention significantly decreases the sample processing time while increasing the number of material samples which can be processed at one time. This invention also improves the environmental ruggedness of the device while significantly decreasing the implementation cost.

Stokes Radiation Time-Multiplexing

Figure 1A:
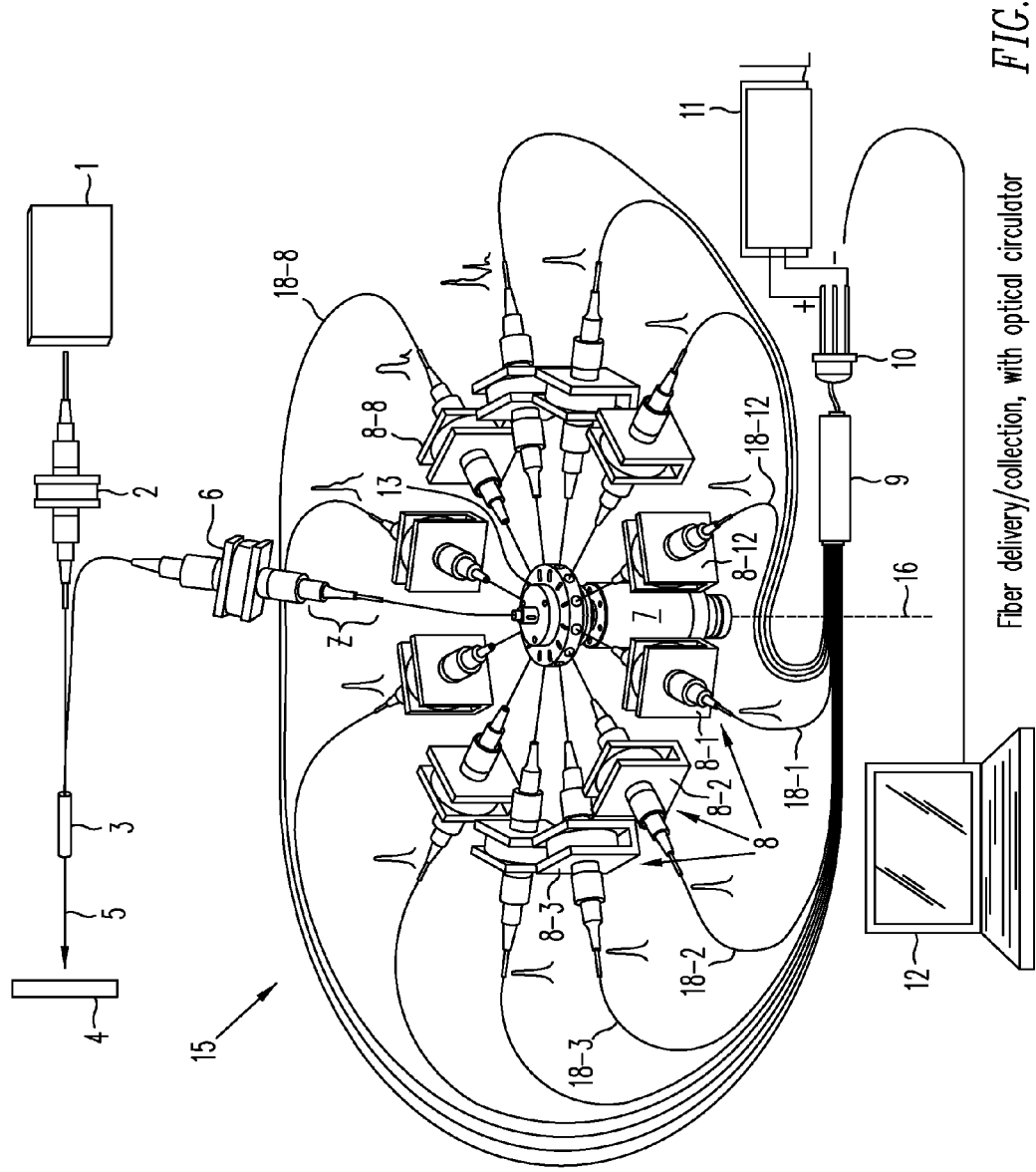
FIG. 1a shows a fiber delivery collection system with an optical circulator in accordance with this invention.

Referring to FIG. 1a, one embodiment of this invention employs a rotary switch such as disclosed in copending patent application Ser. No. 11/185,137 filed Jul. 20, 2005 based on provisional application No. 60/589,454 filed Jul. 20, 2004, both assigned to Neptec Optical Solutions, Inc., the assignee of this application. These two applications are hereby incorporated by reference in their entirety. This rotary switch essentially acts as a time-division multiplexing device.

In the structure of FIG. 1a (which corresponds to the best mode of the invention), light from a pump laser 1 (or other source such as a SLED (a "super-luminescent light emitting diode") or a gas emission lamp using halogen gases or mercury or equivalent) illuminates a material sample 4 to be interrogated. Light back-scattered from the sample (called information light or "Stokes radiation") contains specific information about the chemical and physical make up of the material being interrogated. Hereafter, in this written description, the term "Stokes radiation" will be used to mean the same as "information light", which is light scattered from the sample as a result of light from source 1 impinging on sample 4.

In the embodiment of FIG. 1a, the optical delivery to the sample of the light from the illumination source and the optical collection from the sample of the Stokes radiation are performed through the same fiber 5 (sometimes called a "waveguide"). The light from source 1 to be incident on sample 4 is first passed through narrow bandpass filter 2 to remove spurious radiation outside the desired bandwidth and is then transmitted to the sample through optical fiber 5. Stokes radiation scattered from sample 4 is also carried by waveguide 5 and is directed through an optical circulator 3 to a notch filter 6 to remove spurious information and into the z-axis of the device body. Notch filter 6 blocks the transmission of the residual back-scattered illumination light into the time-division multiplexing device 7. Notch filter 6 can be a multilayer interference filter, a colored glass filter or an absorption cell (typically from an alkali metal vapor such as Rb or Cs). Taken together, the delivery/collection fiber 5, optical circulator 3 and notch filter 6 comprise and will be referred to as the system "probe".

Optical circulator 3 is a well-known optical device with three channels wherein each channel allows the passage of light in a specific direction. In the system of FIG. 1a, circulator 3 lets light pass from the light source 1 to the sample 4 and on the third channel of the circulator 3 lets light scattered from the sample travel back from the sample 4 into the spectrometer and only in that direction. Optical circulators suitable for use with this invention are commercially available from a number of fiber optic device companies such as Optics for Research, located at Caldwell, N.J.

The light from optical circulator 3 is passed through a notch filter 6 which blocks and thus removes light at the main frequency of the light source 1. Filter 6 will pass light at frequencies other than the frequency of light from source 1. The light that passes through filter 6 impacts a motor-driven, rotating prism 13 which can be of a type shown, for example, in copending patent application Ser. No. 11/185,137 filed Jul. 20, 2005 (published as U.S. Publication No. 2006/0072873 A1) incorporated by reference above. The mirrored surface of prism 13 reflects the incoming light through filters 8-1 to 8-12 into one of several waveguides 18-1 to 18-12 arranged circularly in a plane perpendicular to the z-axis of rotation and centered about the z-axis of rotation. While twelve (12) waveguides 18-1 through 18-12 are shown arranged in a circle in a plane around the rotating prism 13, of course, a smaller or larger number of waveguides can be so arranged if desired. For example, in some embodiments 20 to 100 waveguides will be so arranged around the circumference of the rotating prism 13 within a plane to enable the system to determine at least 20 to 100 characteristics of the sample being analyzed.

The rotation of the prism 13 sweeps the Stokes radiation beam across the inputs of the several waveguides 18-1 to 18-12 creating a "time multiplexing" of the single Stokes radiation beam. Thereby, each waveguide receives a time slice of the original optical information signal (i.e. the Stokes radiation). Each waveguide 18-i (where i is an integer varying from 1 to 12 in FIG. 1a or from 1 to N when N filters and waveguides are placed around the circle in the plane perpendicular to the z-axis of rotation) is associated with a specific optical filter 8-i which is selected to transmit only a portion or selected portions of the broad wavelength range contained within the Stokes radiation. Each optical filter 8-i can be, for example, a molecular filter or an interference filter. The filtered Stokes radiation passing into waveguides 18-1 to 18-12 is then directed through multiplexer 9 to a single optical detector 10 and into electronic analytical equipment, such as a computer, 12 for processing.

Electronic pulse generator 11 causes the photo-sensitive element 10 (which might be an avalanche photodetector, a photodiode, a photomultiplier or a micro channel plate, for example, or any other type of photo-sensitive element), to be turned on and activated whenever a signal from waveguide 18-i strikes the photo-sensitive element 10. The pulse generator 11 essentially synchronizes the operation of photo-sensitive element 10 with the arrival of a signal scattered from prism 13 through a corresponding waveguide 18-i.

The filters 8 in front of waveguides 18 are each selected to allow certain light representative of certain types of components which might be present in the sample 4 to be transmitted from the probe to the optical fibers 18-1 through 18-12 to the multiplexer 9. The multiplicity of filters 8-1 to 8-12 spectrally decompose the Stokes radiation and separate it into a timed sequence of pulses. These pulses are re-directed to a single photo-sensitive element 10 via a multiplexing element 9.

Multiplexer 9 (which might be a single mode fiber, a multi-mode fiber, or a photonic crystal fiber (PCF) depending on the desired numerical aperture, bandwidth and transmission loss of the device) will pass the signal being transmitted on the corresponding fiber 18-i when information light scattered from the rotating prism 13 impacts the corresponding waveguide 18-i.

The speed of rotation of prism 13 determines the frequency with which signal processing unit 12 (which might, for example, include a digital signal processor, certain recognition algorithms and a computer for carrying out the processing) receives the signals from each of the waveguides 18-1 through 18-12 on FIG. 1a. By increasing the speed of rotation of the prism 13, the number of samples $S_1, S_2, \ldots S_N$, for example, capable of being processed by the signal processing unit 12 in a given time can be increased provided the speed of processing within processing unit is capable of analyzing the samples as they are delivered to the processing unit 12. The speed of the processing unit 12 can be adjusted by including several processing units in parallel if necessary.

Figure 1B:
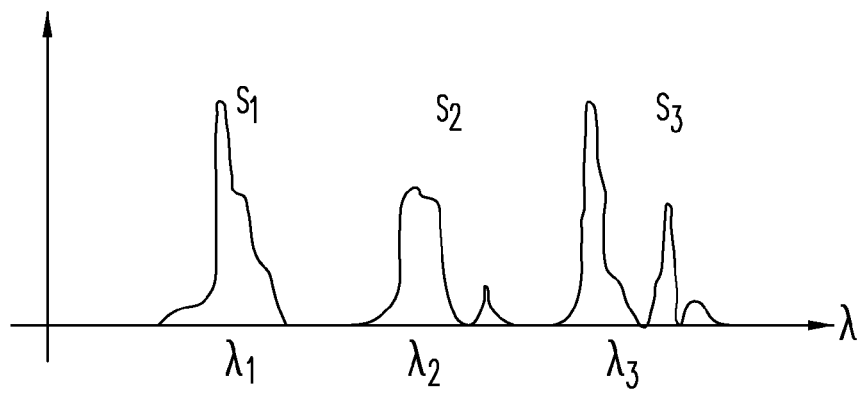
Figure 1C:
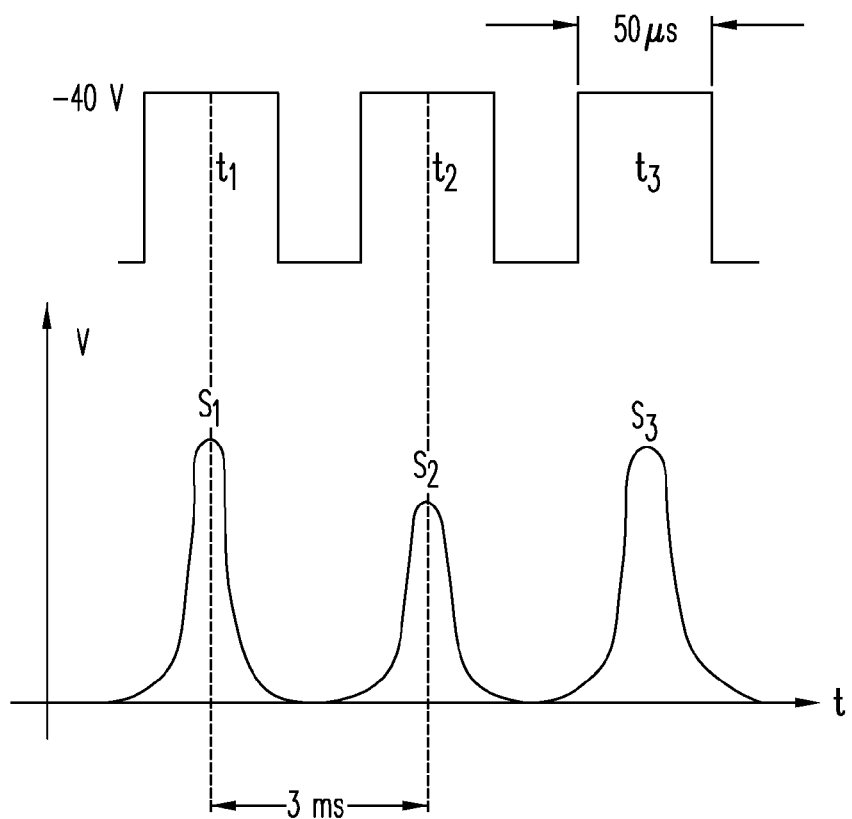

FIGS. 1b and 1c show, respectively, the frequency spectrum of three signals $S_1$, $S_2$ and $S_3$ and the times at which these three signals are made available through waveguides 18-1, 18-2 and 18-3 in sequence (FIG. 1c). As shown in FIG. 1c, each signal $S_i$ reaches an adjacent waveguide 18-i about 3 milliseconds after the preceding signal has reached its waveguide. Thus, if signal $S_1$ reached waveguide 18-1 at time 0, signal $S_2$ would reach waveguide 18-2 at a time 3 milliseconds thereafter and signal $S_3$ would reach waveguide 18-3 at a time 6 milliseconds after the first signal $S_1$ reach waveguide 18-1. Three millisecond time between each of the signals with eight different signals being processed corresponds to 41⅔ revolutions per second. The actual revolutions per second will depend upon the number of samples to be generated which corresponds to the number of waveguides 8 which are employed on the circle in the plane perpendicular to the z-axis of the system shown in FIG. 1a.

Detector Time-Multiplexing

The detector (made up of photo-sensitive element 10, electronic pulse generator and synchronizing circuit 11 and the signal processing unit 12) is electrically turned off and optically isolated until it is required to be active to sense the weak information input signal. The position of the prism 13 with the Stokes radiation relative to a specific waveguide 18-i with filter 8-i is time correlated by electronic synchronizing circuit 11 with the electrical reactivation of the photo-sensitive element 10 in the detector; therefore, element 10 electrically turns on exactly when the Stokes radiation pulse reaches it. This innovation permits accurate signal timing and enables the photo-sensitive element 10 of the detector components 10, 11 and 12 to be at maximum optical sensitivity when light impacts element 10. The combination of the above procedures results in a broad band data collection, within the duration of one rotation cycle of the prism 13.

One implementation employs pump laser 1 illuminating a sample 3 (which might consist of a solid, a liquid, or a gaseous material embedded in a pipeline, container, or in free space) and multi-mode optical fibers 18-1 to 18-12 as waveguides for directing the different light paths. Back-scattered light is connected to an optical collimator 3 (input collimator) which is mounted on top of the device body 15, along the axis of rotation 16 (also called the z-axis) of the time-division multiplexer 7. A 7,000-rpm motor (not shown) with a 7 mm×7 mm prism 13 is surrounded by the array of twelve (12) optical collimators 8-1 to 8-12 robotically aligned and mounted on a ceramic cylindrical shaped body (optical bench). These collimators 8-1 to 8-12 are positioned on a plane perpendicular to both the input collimator 3 and the axis of rotation 16 of the motor shaft.

Along the optical path of each collimator, a wavelength specific filter 8-1 to 8-12 is placed, creating twelve (12) optical "channels". Each channel filters a different region of the input spectrum allowing the detector 10 to sense only the selected wavelengths. The collection of the ceramic body, collimators, filters 8-1 to 8-12 rotating mirrored prism 13, and motor and ancillary structures comprises the rotary optical switch device 15 (FIG. 1a).

The multiple collimators direct the filtered light channels into a detector 10 via multi-mode optical fibers 18-1 to 18-12 whose output signals are multiplexed to impact the surface of a single, ultra-sensitive photodetector device 10 (e.g. an avalanche photo-detector, or APD). The detector 10 is electrically pulsed on and off via a pulse generator 10 and electrically synchronized to the position of the motor shaft, enabling the coordination of the rotating prism 13 with the electrical activation of the photodetector 10. By turning on and off the detector 10, Raman spectroscopy is possible with lower level signals than heretofore used because keeping detector 10 off when no signal light (i.e. Stokes radiation) is incident on the detector 10 keeps the noise level down. This makes it possible for detector 10 to pick up weaker Stokes radiation than in prior art systems.

Different types of detectors 10 can be used. A highly sensitive APD can be used (typically Si, GaAs or InGaAs material type, depending on the wavelength region to be measured), operated marginally (3-4%) above the internal breakdown-voltage of the device (~40 V) to minimize noise and maximize sensitivity to light (Geiger-mode operation).

Other embodiments can use photomultiplier tubes, to operate in the UV-visible spectral range. By sending only selected, pre-filtered light into the detector 10 and by only powering the detector 10 when the light pulse is about to impact detector 10, an overall reduction in both electrical and optical noise of significant magnitude is achieved allowing for a collection of spectral information which is 2-3 orders of magnitude faster than conventional techniques. The rotary optical switch 15 combined with the optics 10 and electronics 11, 12 described above provides a vastly improved Raman spectrometer instrument.

The signal from the photosensitive element 10 is amplified, filtered, and processed electronically by signal processing unit 12. Signal processing can be performed by analog or digital electronics, or a combination of both. A digital signal processor (DSP) can be implemented as a very compact and fast device to perform such operations. The combination of multiplexing element 9, photo-sensitive element 10, pulse generator 11, and signal processing unit 12 will be called the "back end" of the Raman spectrometer system described herein.

An additional embodiment uses a pump laser through a multi-mode fiber that also acts as a collection mechanism where the return spectra is separated from the transmitted spectra via the use of a circulator or equivalent.

Figure 2:
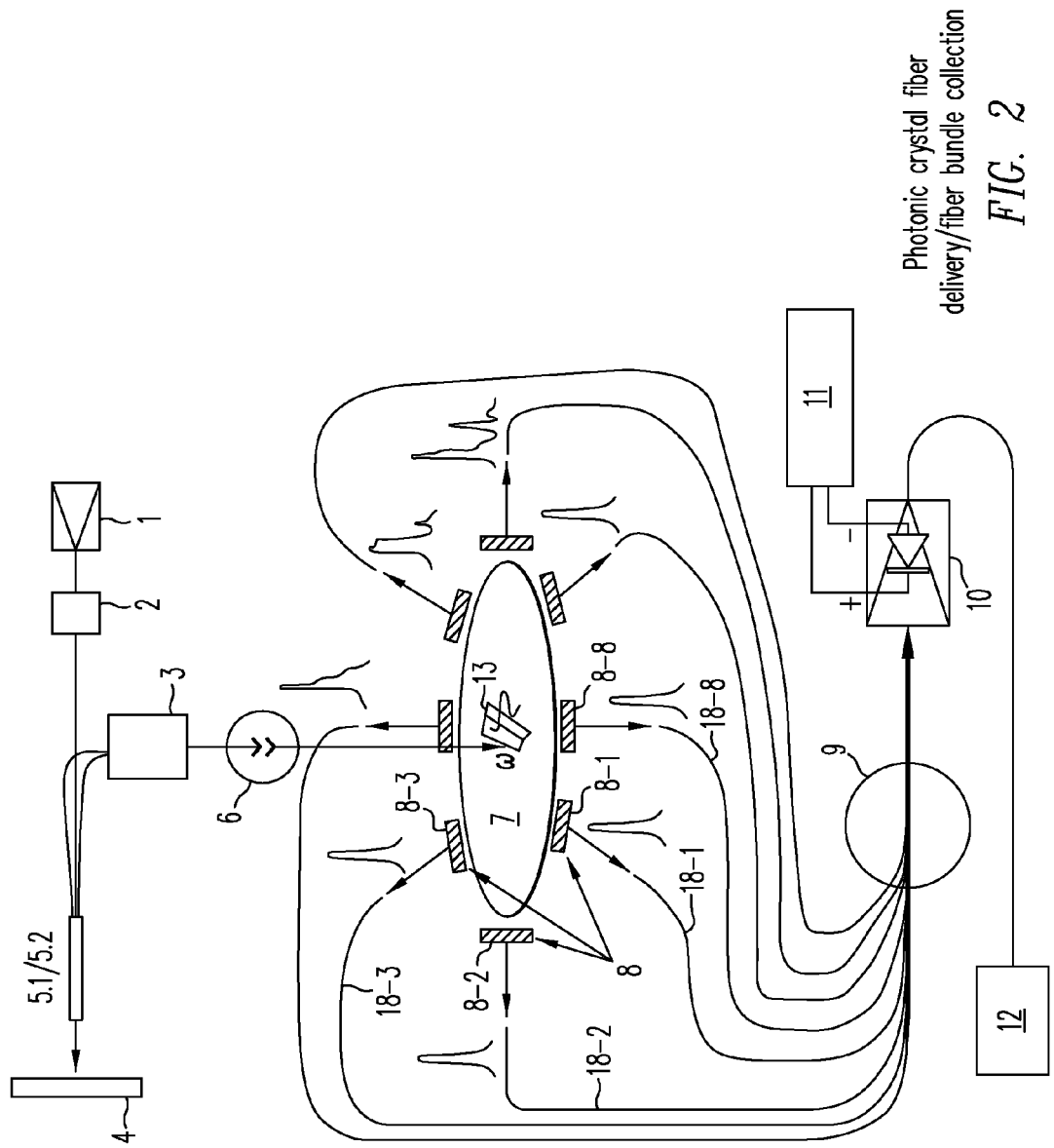
FIG. 2 shows a photonic crystal fiber delivery system in accordance with this invention.

FIG. 2 shows a photonic crystal fiber delivery system using a fiber bundle collection. In FIG. 2, many of the components are the same as or similar to those in FIG. 1a but for simplicity will be shown schematically rather than in the detail shown in FIG. 1a. (A similar approach is taken with respect to the remaining FIGS. 3, 4, 5a, 5b and 6.) The system of FIG. 2 uses a different probe than the system in FIG. 1a. The probe of the system in FIG. 2 delivers the light from the illumination source 1 to the sample 4 by one optical fiber and collects the Stokes radiation scattered from the sample 4 by different optical fibers. The delivery of the light to sample 4 is done by a photonic crystal fiber to reduce the modal area of illumination on the sample 4. The Stokes radiation is delivered by a set of optical fibers around the delivery fiber to maximize the efficiency of collection of the Stokes radiation. Multiplexer 3 collects the signal from the fiber bundle and directs it to the notch filter 6, the time division multiplexer 7, the filers 8, a second multiplexer 9 and the photosensitive element 10. The remainder of the back end is similar to what is shown in FIG. 1a and includes the electronic pulse generator 11 and the signal processing unit 12. Another difference between the system of FIG. 1a and the system of FIG. 2 is the use of multiplexer 3 in the optical channel between the scattered light from the sample 4 and the notch filter 6 located in the path followed by the Stokes radiation to prism 13 in the time-division multiplexing device 7. The numbers set forth in the remainder of the structure in FIG. 2 are identical with the numbers set forth in FIG. 1a to the extent these components are the same. Therefore, these components operate as described in connection with FIG. 1a.

Figure 3:
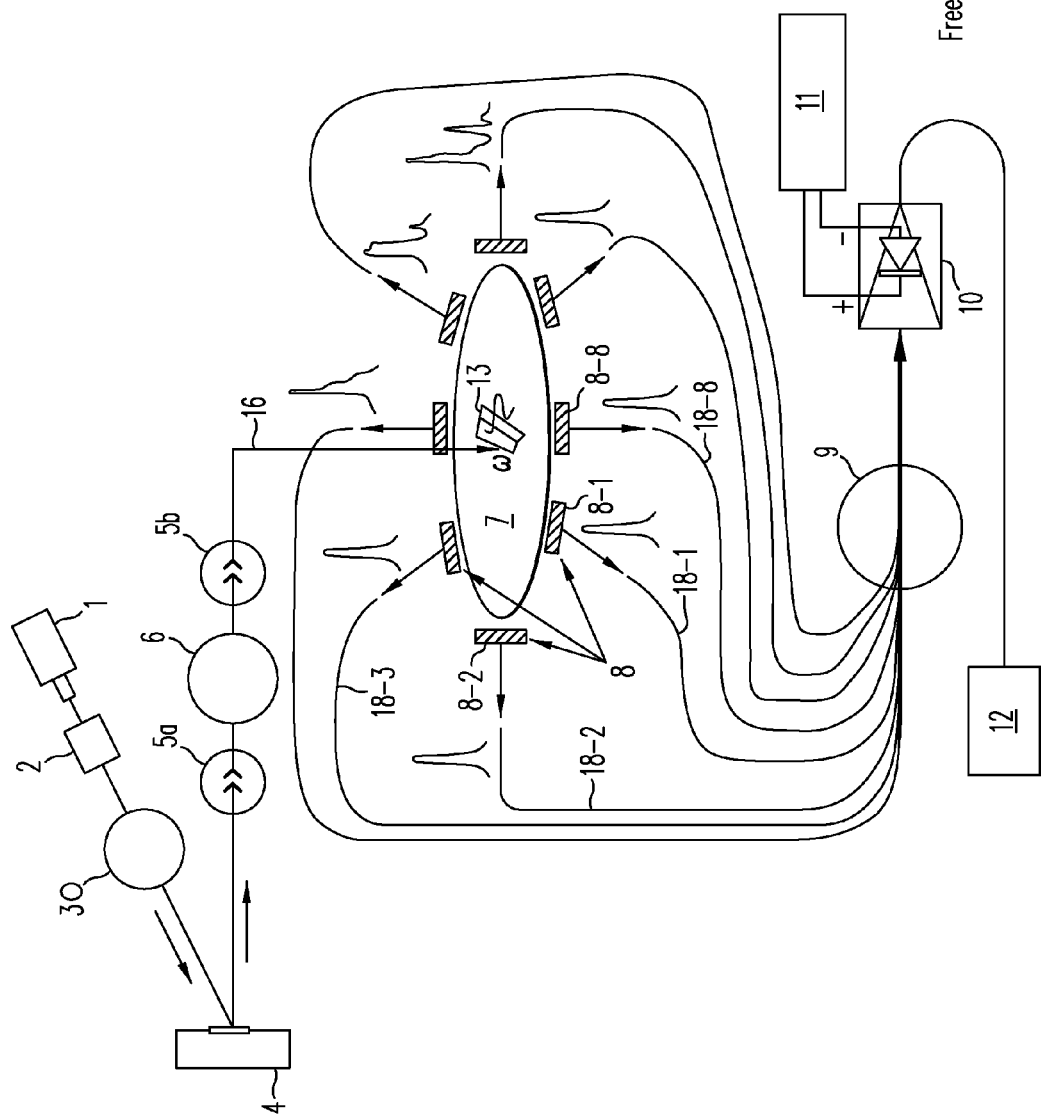
FIG. 3 shows a free space delivery and collection system in accordance with this invention.

FIG. 3 shows a system which uses a probe which includes a free space delivery component. The system shown in FIG. 3 includes many of the components shown in FIGS. 1a and 2. Unless otherwise specified, identical components are numbered identically as in FIGS. 1a and 2. New components are numbered differently. The system shown in FIG. 3 can be used in near field collection (microscopy) or far field collection (remote sensing) regimes.

In FIG. 3, an illumination source 1, which could be a laser or bright lamp, for example, provides light (such as CW pump radiation) which passes through narrow bandpass filter 2 to free space delivery optics 30 which could be a lens, a parabolic mirror or similar structure. From optics 30, the focused light impacts on sample 4 at a selected position. The scattered light (i.e., the Stokes radiation) passes through notch filter 5a (which could be, for example, an interference grating, colored glass, an absorption cell or a fiber grating). Notch filter 5a, if desired, can be embedded in fiber or located in free space.

The signal from notch filter 5a is then transmitted in free space to collection optics 6 (which might include appropriate combinations of selected ones of lenses, mirrors, prisms and apertures, for example). Optics 6 couples the scattered Stokes radiation into an optical fiber 16 that directs the light to the time-division multiplexing device 7 (as described above). At least part of optical fiber 16 is located on the axis of rotation of the time division multiplexing device 7. Notched filter 5a can, if desired, be replaced by an identical notched filter 5b located after optics 6 rather than before optics 6.

Prism 13 reflects the light transmitted along optical fiber 16 to an appropriate one of filters 8-1 through 8-8. Filters 8-1 through 8-8 can be any one of a number of different types of filters such as molecular filters, or interference filters, for example as described above in conjunction with FIG. 1a and FIG. 2. The signals from filters 8-1 through 8-8 are sent on optical fibers 18-1 through 18-8 to a multiplexer 9 where each of the signals then is transmitted to light detector 10. Electronic synchronization circuit 11 activates light detector 10 before each of the signals from the corresponding filters 8-1 through 8-8 reach detector 10 and thus synchronizes the turning on of detector 10 with the application of the signal scattered by prism 13 to the appropriate one of filter 8-1 through 8-8.

The system otherwise operates just as the system shown in FIGS. 1a and 2.

Figure 4:
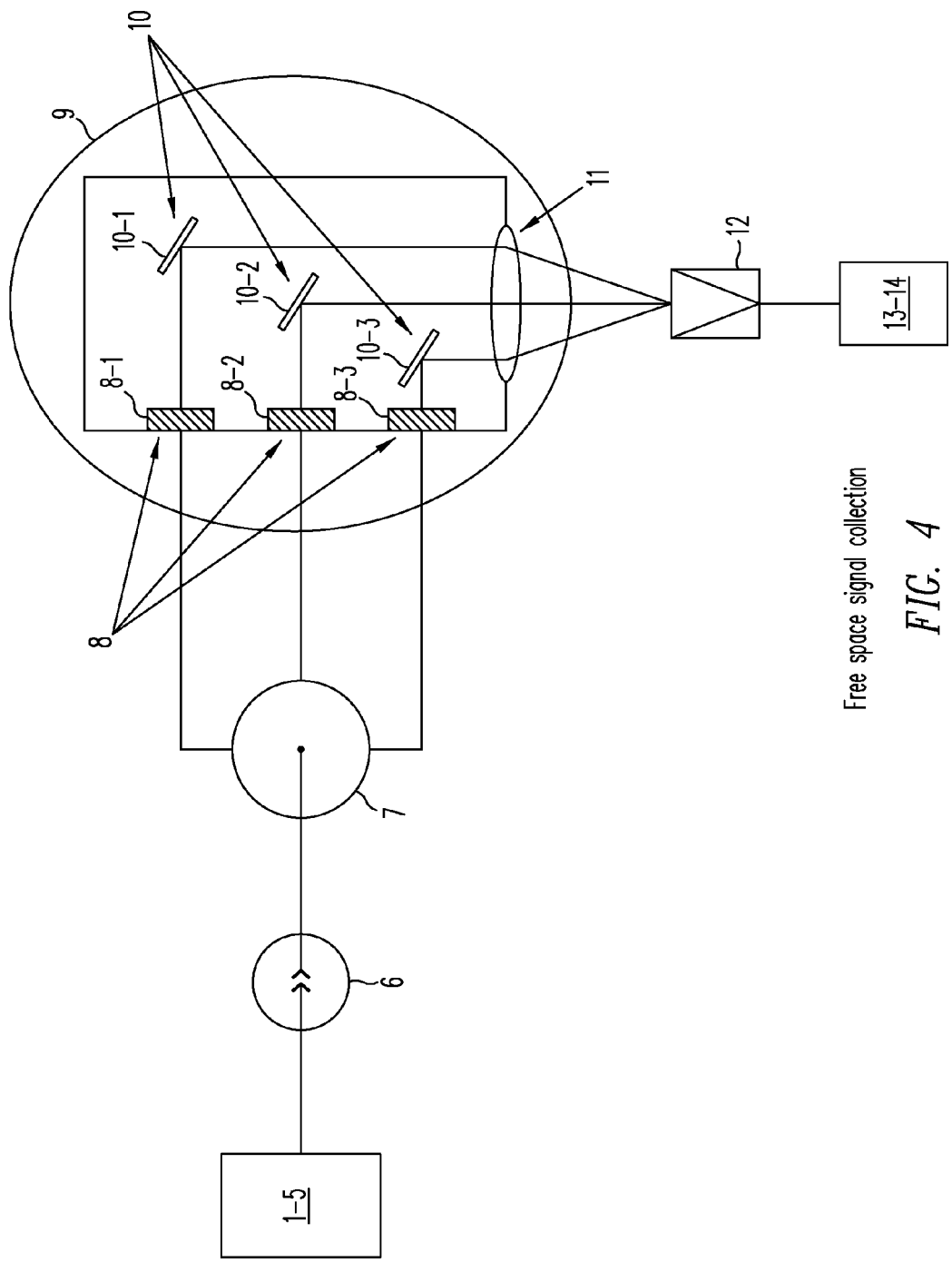
FIG. 4 shows a free space signal collection system utilizing the principles of this invention.

FIG. 4 shows another embodiment of this invention with a modified back end. An illumination source 1 (which can be a laser or bright lamp, for example), a narrow bandpass filter 2, a multiplexer (which is of a well-known construction) 3, a sample 4 and a delivery fiber 5 (which, for example, can be a photonic crystal fiber (PCF)) operate in much the same way as shown in FIGS. 1a, 2 and 3. In FIG. 4, these components are depicted in the box with the numbers 1 to 5. The information signal scattered from the sample 4 is transmitted to the notched filter 6 (which again can be an interference grading, colored glass or an absorption cell, for example) and then to time-division multiplexing device 7. The time-division multiplexing device 7 can be, for example, the rotating disk with a prism 13 on it as shown in FIGS. 1a, 2 and 3. From this disk, however, the signal is sent in a manner described above in conjunction with FIGS. 1a, 2 and 3 to various molecular or interference filters 8-1, 8-2 and 8-3 as shown. Of course, other numbers of filters can be used if desired. Each filter 8-1, 8-2 and 8-3 is arranged in a structure known as a free space multiplexer box 9 which can be fabricated of any acceptable material such as ceramic, metal, or plastic. For example, Box 9 contains reflecting elements 10-1, 10-2, and 10-3 (for example, mirrors) for reflecting the corresponding signals from filters 8-1, 8-2 and 8-3, respectively, to a focusing lens 11. The signal from lens 11 then is sent to a photo-sensitive element 12 which operates as described in the previous description of system shown in FIGS. 1a, 2 and 3. The detector 12 sends its signal to the signal processing unit 14. Electronic pulse-generator and synchronization circuit 13 operates to turn on the detector 12 in response to the signals from multiplexing device 7 hitting the respective ones of mirrors 10-1 through 10-3 and thereby in time sequence as shown in FIG. 1c striking detector 12. The system in this respect operates as described above.

FIG. 5a illustrates a system for Raman spectroscopy which employs multiple lasers. Thus, multiple lasers 1-1, 1-2 and 1-3 provide signals of different wavelengths $\lambda_1$, $\lambda_2$, $\lambda_3$, respectively. These signals are transmitted to a time-division multiplexer which has thereon an optical system which allows these signals to be transmitted in sequence to a sample 4. The Stokes radiation scattered from sample 4 is sent to optical circulator 3 and from there is sent to a block filter 5 which blocks the signals with wavelengths $\lambda_1$, $\lambda_2$, and $\lambda_3$ but which passes the stokes radiation associated with these wavelengths. Optical filter 5, although a blocking filter for the wavelengths $\lambda_1$, $\lambda_2$, and $\lambda_3$, is a single bandpass or band-block filter for the Stokes radiation. This combined filter is made possible by the large spectral range between the illumination radiation and the Stokes radiation in most Raman signals.

Photo-sensitive element 6 then receives in sequence Stokes radiation signals associated with wavelengths $\lambda_1$, $\lambda_2$, $\lambda_3$ and is readily turned on in synchrony with the operation of time-division multiplexer 2 to transmit the signals to a processing unit 12 which operates as described above in conjunction with FIGS. 1a, 2 and 3.

FIG. 5b shows a similar structure as in FIG. 5a except here a single broadband light source 1 (for example, a metal-halogen light source, or a Mercury gas lamp, or a Xenon arc lamp, or a Neon arc lamp) provides light which is then transmitted through filters 3-1, 3-2 and 3-3 which are part of time-division multiplexer 2. As time-division multiplexer 2 rotates, specific pulses of light are passed along the path from multiplexer 2 to sample 5 in a reverse direction from the direction of the light transmitted in the systems shown in FIGS. 1a, 2, 3, 4 and 5a. The Stokes radiation scattered from sample 5 is passed through optical circulator 4 and then through a filter 6 which passes $\lambda_1$, $\lambda_2$ and $\lambda_3$ to the photo-sensitive element 7. Photo-sensitive element 7 is again activated by the electronic pulse generator 11 (not shown in FIG. 5b) which synchronizes the turning on of detector 7 with the incidence of the light from filters 3-1 through 3-3 on sample 5. Processor 12 (also not shown in FIG. 5b) then processes the output signal from detector 7 to determine the presence of selected components in the sample.

FIG. 6a illustrates a structure which provides coarse and fine spectral coverage. Collected and filtered light from the sample 4 is passed through a time-division multiplexer 21 which operates as discussed above in conjunction with FIGS. 1a, 2 and 3. Collimators 31-1 to 31-M (where M is an integer representing the number of correlators in multiplexer 21) send this light to auxiliary channels. Then a drum with a coarse set of filters 41-1 to 41-P and a fine set of filters 42-1 to 42-Q, where P and Q are each a selected integer representing the maximum number of coarse and fine filters, respectively, is inserted into the multiplexer 21 such that the light reflected from the prism 31 in time-division multiplexer 21 is then sent through in time sequence each filter in the coarse set of filters 41-1 to 41-P to provide a broadband sensitivity to light. By further inserting the drum into multiplexer 21, a narrow set of filters 42-1 to 42-Q which provide a narrow band sensitivity to light, is placed between the rotating prism 13 and the transmission channels to the light detector. The bandwidth associated with the coarse set of filters 41 is shown in FIG. 6b within the bracketed range "A" whereas the bandwidth associated with the fine set of filters 42 is shown bracketed with the range "B" in FIG. 6b. This particular structure allows the system to make a fast determination that there is a signal of interest within the broadband "A" and then determine using the fine set of filters whether or not that signal of interest actually contains information with respect to a component of interest.

Figure 6:
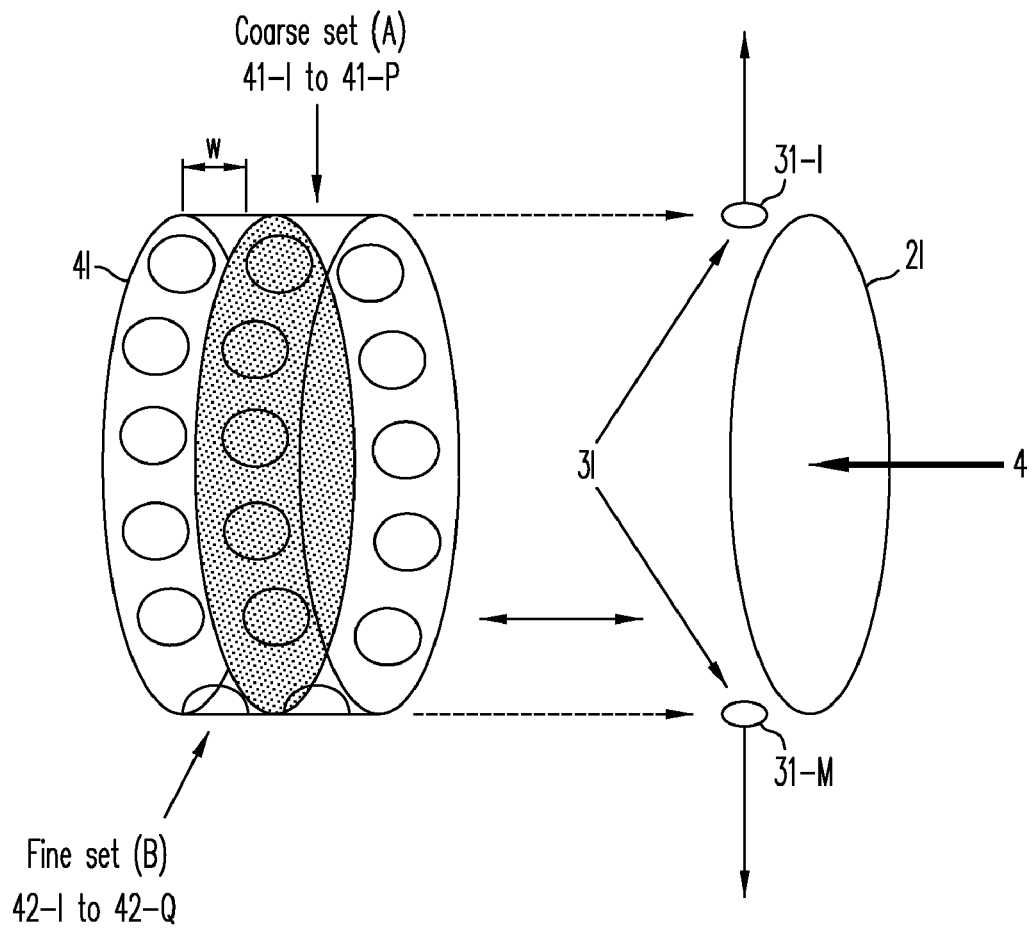
FIG. 6 shows a technique for implementing coarse and fine spectral coverage.
Figure 6:
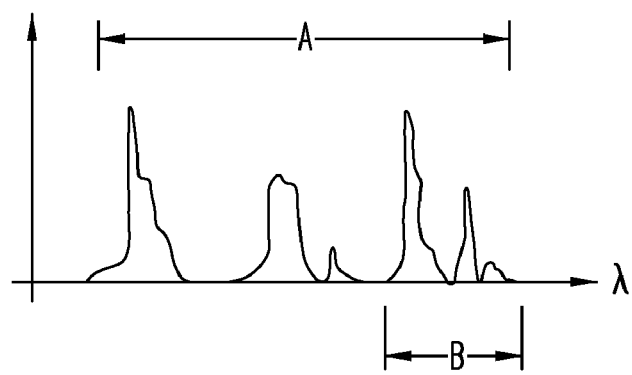

The drum shown in FIG. 6 has two sets of filters, but more than two sets of filters can be employed in this embodiment if desired. The use of a plurality of filter sets allows the system to cover a wider spectral range in the Stokes radiation domain or possibly to increase the spectral resolution for a given feature as discussed above.

The particular set of filters to receive the light from the multiplexer 21 is moved into position by moving the drum on which the filters are mounted laterally along its cylindrical axis by means of mechanical components of well known design but not shown here for clarity. The coarse set of filters or the fine set of filters are actually moved laterally along the z-axis of the time division multiplexer 21 until the particular ring of filters (either coarse or fine) is spaced precisely between the collimators 31-1 through 31-M and the rotating prism 13 associated with the time division multiplexer 21. As a result, as the time division multiplexer rotates, the beam from the prism 13 is filtered through either the coarse set or the fine set of filters and the particular collimator associated with each of the filters in the coarse set or the fine set will then pass the signal through the corresponding waveguide to the signal processing structure as described above, such as to processor 12 in FIG. 1a. Of course, the width W of each band of filters (i.e. the width of the coarse set 41-1 to 41-P and the width of the fine set 42-1 to 42-Q must be such that when taken together, the distance of the collimators 31-1 through 31-M from the plane of the time division multiplexer 21 on which the collimators 31 are mounted is sufficient to allow the fine set of filters 42-1 to 42-Q to actually be located between the collimators 31 and the rotating prism 13 such that the signal from the rotating prism 13 will in fact impact appropriately on each filter in the fine set of filters.

The system shown in FIG. 6 is highly convenient in applications where a layered response is necessary in order to activate an alarm, as in the case where the presence of a noxious substance is ultimately verified by a refined spectral analysis.

Description of the Data Processing Algorithm

The algorithm used for processing the electrical signal from the photosensitive unit is a discrete principal component analysis procedure (dPCA) which will be outlined in the following. The amount of Raman power, $P_R(v_i)$, produced by frequency mode, $v_i$, from a given scattering material, upon the incidence of pump radiation with power, $P_P$, is given by the following expression $$P_R(v_i) = P_P \cdot \varepsilon \chi_i \rho l \left(\frac{\partial \sigma}{\partial \Omega}\right)_{\lambda_R} \Delta \Omega \qquad (1)$$

where, $\epsilon$, is the optical collection efficiency of the system, $\chi_i$ is the relative concentration of the scattering substance (a number between 0 and 1), and $\rho$, is the density of the scattering substance (g/cm$^3$), 1, is the transversal dimension of the illumination area of the sample, $(\partial \sigma/\partial \Omega)_{\lambda_R}$, is the Raman scattering cross section of the material (in cm$^2$/(gSr)), and $\Delta \Omega$ is the total solid angle of collection.

For the quantitative determination of a mixture with m different substances, assume that n different Stokes Raman spectral bands have been selected for the channels of the time-division multiplexing device. The number n has to equal or be greater than m, its exact value being application specific. Normally, n will range between just a few (3 or 4), and several tens of channels (50 to 100). The judicious selection of a limited number of spectral bands is essential for the discretization of the analysis technique to make it simple. Typical PCA algorithms make use of the whole spectrum across a broad collection band, with 100-1000 values per spectrum. Due to the lower dimensionality of the data sets (by a factor of 10-100), the number of operations to complete the algorithm is 3 to 6 orders of magnitude lower than for conventional algorithms. If $\sigma_{ij}$ denotes the normalized contribution of the Raman spectrum from substance j onto filter i, and $\chi_i$ is the relative concentration of substance j in the mixture, then the collected light intensity by the switch at channel k, $A_k$, is:

$$A_k = \sum_l \sigma_{kl} \chi_l \quad (2)$$

The validity of Eq. (2) in the case of a Raman spectrum is supported by the linear dependence on the concentration, $\chi_j$, expressed in Eq. (1). The same statement is not true in the case of Infra-red absorption, and complicates the analysis in the case of high analyte concentrations. In general, Eq. (2) is a system of n inhomogeneous linear equations with m unknowns. The basic proposition of chemometrics is that it is always possible to find enough independent bands, n, in the Raman spectra of the substances of interest, so that Eq. (2) can be solved for $\chi$. Following the spirit of Chemical Factor Analysis,[1] we can write Eq. (2) in matrix notation as

[1] Edmund R. Malinowski; Factor Analysis in Chemistry, 3rd Edition, Wiley-Interscience, New York (2002). ISBN 0-471-13479-1.

$$A = \sigma \cdot \chi \quad (3)$$

where, $\sigma$, is an n×m rectangular matrix. A new matrix, Z, is defined:

$$Z = \sigma^t \cdot \sigma \quad (4)$$

Z is a square, symmetric matrix, and therefore it can be diagonalized and inverted by a unitary matrix, Q, as in:

$$Z = Q^t \cdot \Lambda \cdot Q \quad (5)$$

where, $\Lambda$, is a diagonal matrix containing the eigen values of Z. Finally, from Eq. (3), (4) and (5), a solution can be found for $\chi$ as $$\chi = Q \cdot \Lambda^{-1} \cdot Q^t \cdot \sigma^t \cdot A \quad (6)$$

The matrix of eigen values, $\Lambda$, is relevant because it dissects the parameter space, $\chi$, in terms of linear combinations of its components such that their net effect in the measurement, A, can be quantified. This is accomplished by evaluating the relative magnitude of the eigen values ($\Lambda_i$). The parameter(s) that has the highest value indicates the relevant variable(s) in the problem, whereas the others give an indication of the dispersion of the data around the qualifying parameter(s).

Equation (6) is basically the equation that is used in the signal processing unit 12 to calculate the concentration of each analyte (i.e. the concentration of each different component in the sample) from the information represented by A. Each entry in vector A corresponds to a photodetector measurement from a particular waveguide connecting to the photodetector 10 (FIG. 1a) when a signal from a particular filter 8-i is impacting on detector 10. Thus, this particular signal as produced by detector 10 will be processed by processing unit 12 using constants which have been placed in a table in memory for access by computer 12, together with all other signals from each filter 8-i, after each cycle of the time-division multiplexing device is completed. The user would identify the particular sample being analyzed and the computer then would automatically go to a table corresponding to the possible components of that sample to determine the constants $Q \cdot \Lambda^{-1} Q^t$ and $\sigma^t$ to be used in the calculation of the concentration of each analyte which constitutes the sample. Q and $\sigma$ depend on the particular filters selected. An example set forth below will explain what the units are for each of these symbols and give therefor a calculation as would be done by signal processing unit 12 based upon a typical sample to be analyzed by the system. Example 1.

The construction of the matrix, $\sigma$, starts by selecting n bandpass filters, $f_i$, with bandwidth $\Delta\lambda_i$. The elements of the matrix are thus given by the following expression:

$$\sigma_{ij} = \kappa \int_{\lambda_i - \Delta\lambda_i/2}^{\lambda_i + \Delta\lambda_i/2} f_i(\lambda) \cdot g_j(\lambda) d\lambda; \quad (7)$$

where $f_i$ is the pass-band function for filter i, and $g_j$ is the wavelength-dependent Raman efficiency for substance j, including all its active Raman bands. The factor, $\kappa$, is a constant that relates the unit-less numbers, $\chi_j$, to the photodetector measurements, $A_i$, in Watts, through Eq. (3). Two fundamental issues are: the number of filters to be used, and which filters to use, $f_i$ in terms of their center wavelength, $\lambda_i$, and their bandwidths, $\Delta\lambda_i$. For a given number of filters, n, the error in measurement can be proven to be inversely proportional to $\sqrt{\xi^2}$, with $\xi = \text{Det}(Z)$. Therefore, the essential step of the dPCA technique[2] comprises the selection of a filter set {f1, f2, ..., fn} such that $\xi$ is maximized, for a given n, resulting in a value $\xi_n$. It can also be proven that $\xi_n$ grows monotonically with n. The final decision of the number of filters to be used, n, is made as a compromise between the tolerance level for the measurement error, and the architectural considerations for device construction.

[2] Real-Time Broad-Band Measurement of Cholesterol, Collagen, and Elastin Using a Novel Rotary Switch Spectrometer; Ricardo Claps, Roy Guynn, Wiktor Serafin, Jeff Virojanapa, Aaron Urbas, and Robert A. Lodder *Proc. SPIE* 6078, 60782G (2006).

EXAMPLE

Figure 7:
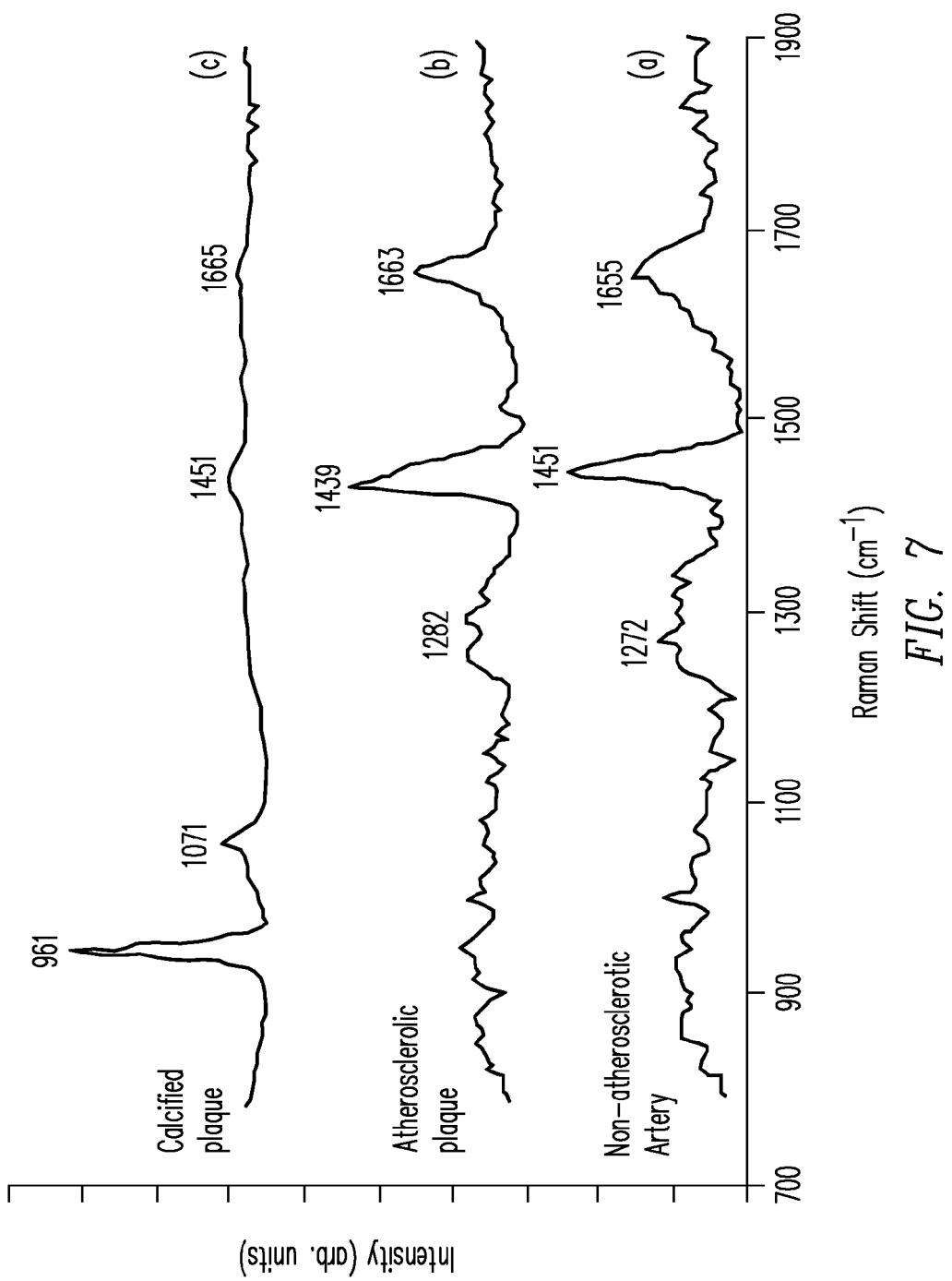
FIG. 7 shows Raman spectra of compounds identified in the human carotid artery.

As an illustration of the procedure mentioned above, a description of a specific example will be sketched in this paragraph. Let us consider the problem of cardiovascular angiography. The substances of interest in this case are Cholesterol, Collagen and Elastin (Ch, C, and E), FIG. 7 shows the characteristic Raman spectra for these compounds. Table I shows the details of the spectra, to be used in the calculations.

TABLE I

Stokes Raman spectra of Collagen, Elastin and Cholesterol

| Substance | Frequency Band (cm$^{-1}$) | Cross Section (×10$^{-9}$ cm$^2$/gSr) |
|---|---|---|
| Collagen | 1668 | 1.39 |
| Elastin | 1664 | 1.7 |
| Cholesterol | 1440 | 4.44 |

Information from Ref. [a, b]. Pump wavelength is $\lambda_p = 1064$ nm Due to the uncertainty or variability in Molecular Weight of large bio-polymers, the cross-section is more adequately expressed in mass (g).
[a] J. M. Dudik, C. R. Johnson, S. A. Asher; "Wavelength dependence of the preresonance Raman cross sections of CH$_3$CN, SO$_4^{2-}$, ClO$_4^-$, and NO$_3^-$", J. Chem. Phys. 82 (4) 1732 (1985).
[b] R. Manoharan, J. J. Baraga, M. S. Feld, R. P. Rava; "Quantitative histochemical analysis of human artery using Raman spectroscopy", J. Photochem. Photobiol. B: Biol. 16 211 (1992).

The construction of the matrix, $\sigma$, begins by selecting 3 filters, whose specifications are listed in Table II below.

TABLE II

| nm | $f_1$ | $f_2$ | $f_3$ |
|---|---|---|---|
| Center λ | 1258 | 1294 | 1229 |
| Δλ | 1.2 | 0.2 | 2.0 |

Using Eq. (7), matrix σ becomes $$\sigma = \begin{pmatrix} 0.330 & 0.210 & 0.226 \\ 0.228 & 0.303 & 0.219 \\ 0.003 & 0.055 & 0.121 \end{pmatrix}$$

And from Eq. (4) we have:

$$Z = \begin{pmatrix} 0.160 & 0.137 & 0.124 \\ 0.137 & 0.137 & 0.119 \\ 0.124 & 0.119 & 0.114 \end{pmatrix}$$

The decomposition of z takes place by matrices Λ and Q (Eq. (5)), given by:

$$\Lambda = \begin{pmatrix} 0.393 & 0 & 0 \\ 0 & 0.013 & 0 \\ 0 & 0 & 0.005 \end{pmatrix}$$

$$Q = \begin{pmatrix} -0.707 & -0.690 & -0.156 \\ 0.608 & 0.480 & 0.633 \\ 0.362 & -0.542 & 0.758 \end{pmatrix}.$$

Once the matrices shown above have been constructed, the implementation of the algorithm in the Raman device is quite simple: The set of power readings obtained in one cycle of the time-division multiplexer with the photodetector comprises the measurement vector A. This vector is introduced in Eq. (6), with σ, Λ and Q as shown above, to obtain the concentration vector, $\chi$.

Figure 8:
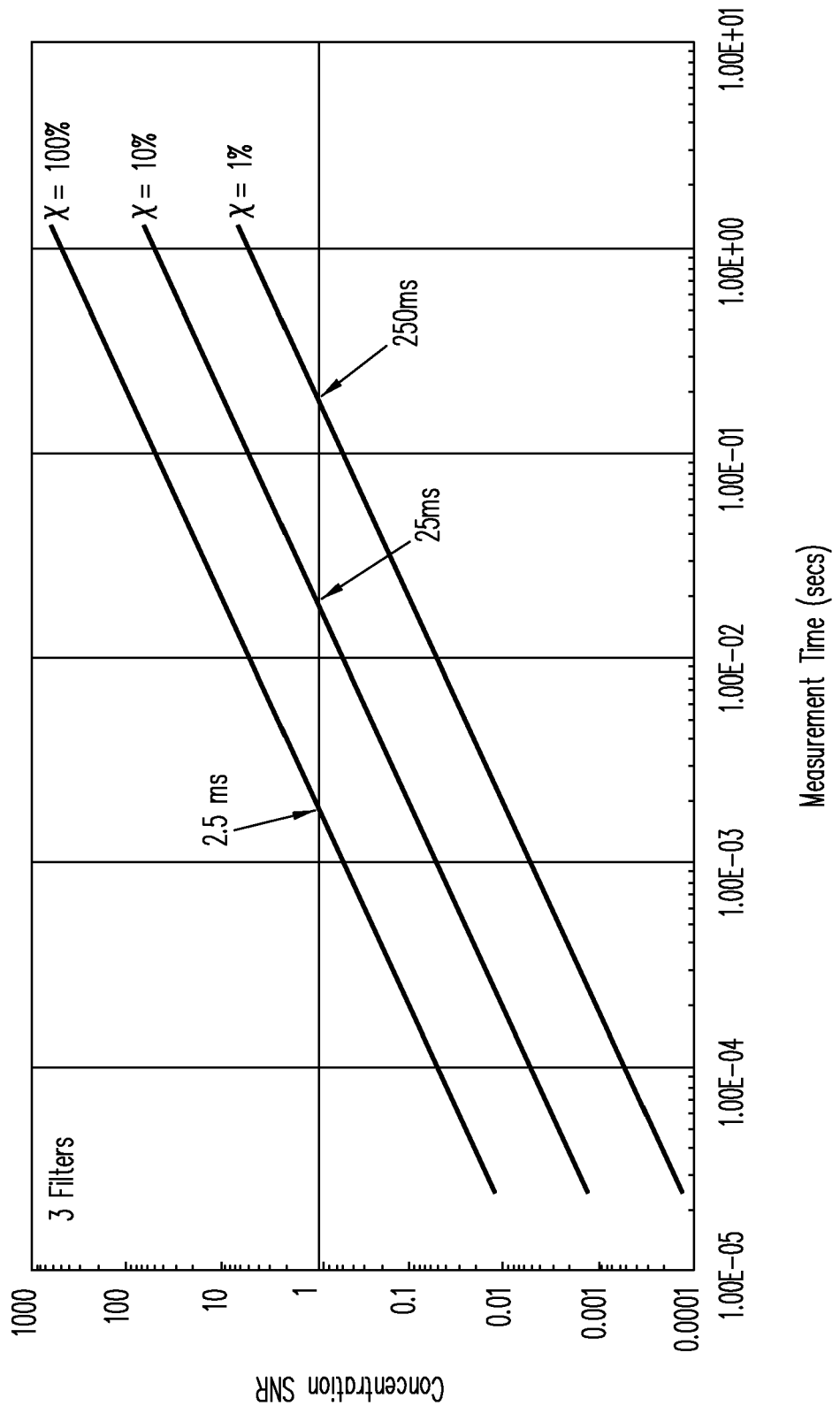
FIG. 8 shows the concentration signal to noise ratio as a function of measurement time for different concentrations of the compounds shown in FIG. 7.

The result of using the previously chosen set of filters for the specific task of measuring Cholesterol, Collagen and Elastin is shown in FIG. 8. FIG. 8 displays different curves for the Signal-to-Noise ratio (SNR) of the concentration measurement, as a function of the measurement time of the Raman device. Clearly, for larger concentrations the SNR is higher, allowing for a faster measurement of the sample. As the concentrations are reduced, the SNR approaches the limiting value of 1, so longer measurement periods are needed in order to obtain a precise measurement.

The above description is illustrative only. Those skilled in the art will recognize other embodiments of the invention which can be implemented in view of this disclosure. As technology advances, other embodiments of this invention will be capable of being implemented. The claims are intended to cover all these possible embodiments.

What is claimed is:

1. A Raman spectroscopy system comprising:
a light source for producing light to be directed at a sample;
a time-division multiplexing device for taking Stokes radiation scattered from the sample as a result of said light impinging on said sample and distributing that Stokes radiation to each of a plurality of filters;
a light transmission channel from each of the filters to a detector;
a synchronizing circuit for turning on said detector at the time that a signal from said multiplexing device is expected at said detector; and
analysis means connected to said detector for processing each signal from said detector to detect selected information in each signal.

2. The system of claim 1 wherein said synchronizing circuit synchronizes the turning on of said detector with the arrival at said detector of a signal from said time-division multiplexing device.

3. The system of claim 1 wherein said synchronizing circuit synchronizes the turning on of said detector with the arrival at said detector of a signal from said time division multiplexing device so as to maximize the sensitivity of the system.

4. The system of claim 1 wherein said synchronizing circuit synchronizes the turning on of said detector with the arrival at said detector of a signal from said time-division multiplexing device so as to reduce the dark count and noise level present at said analysis means.

5. The system of claim 1 wherein said synchronizing circuit synchronizes the turning on of said detector with the arrival at said detector of a signal from said time-division multiplexing device so as to both maximize the sensitivity of the detector and reduce the dark count and the noise level at the analysis means.

6. The system of claim 1 wherein said analysis means is configured to utilize what is known as a discrete principle component analysis procedure to analyze the signals from the detector to determine the nature of one or more analytes in the sample.

7. The system of claim 6 wherein said discrete principle component analysis procedure is specifically configured to enable the analysis means to detect two or more analytes in said sample in one cycle of rotation of the time division multiplexing device.

8. The system of claim 6 wherein said discrete principle component analysis procedure is specifically configured to enable the analysis means to detect two or more discrete multiple analytes in said sample in one cycle of rotation of the time division multiplexing device.

9. The system of claim 1 including:
means for holding said sample such that said light can impinge on said sample.

10. A Raman spectroscopy system comprising:
a time-division multiplexing device for distributing Stokes radiation scattered from a sample as a result of light impinging on said sample to each of a plurality of transmission channels;
a light detector for detecting the Stokes radiation passed by each of said transmission channels
a synchronizing circuit for turning on said detector when Stokes radiation from said multiplexing device is expected at said detector; and
a plurality of filters formed on a one-to-one basis as a part of said plurality of transmission channels.

11. The system of claim 10 further comprising:
analysis means for processing a signal from said detector when said detector is impacted by Stokes radiation to detect selected information in said Stokes radiation.

12. The system of claim 10 further comprising:
a source of said light; and
means for causing said light to impinge on said sample so as to create said Stokes radiation.

* * * * *